United States Patent
Groth et al.

[11] Patent Number: 6,107,518
[45] Date of Patent: Aug. 22, 2000

[54] PREPARATION AND USE OF IMINODISUCCINIC ACID SALTS

[75] Inventors: Torsten Groth, Odenthal; Winfried Joentgen, Köln; Paul Wagner, Düsseldorf; Frank Döbert, Köln; Eckhard Wenderoth; Thomas Roick, both of Leverkusen, all of Germany

[73] Assignee: Bayer Aktiengesellschaft, Leverkusen, Germany

[21] Appl. No.: 09/381,792

[22] PCT Filed: Mar. 23, 1998

[86] PCT No.: PCT/EP98/01670

§ 371 Date: Sep. 24, 1999

§ 102(e) Date: Sep. 24, 1999

[87] PCT Pub. No.: WO98/45251

PCT Pub. Date: Oct. 15, 1998

[30] Foreign Application Priority Data

Apr. 4, 1997 [DE] Germany .................. 197 13 911

[51] Int. Cl.[7] .................................... C07C 229/00
[52] U.S. Cl. ............................................. 562/571
[58] Field of Search .............................. 562/571

[56] References Cited

FOREIGN PATENT DOCUMENTS 0 831 165  3/1998  European Pat. Off. .
1306331    2/1973  United Kingdom .

OTHER PUBLICATIONS

Database WPI, Sec. Ch, Wk 9507, Derwent Pub. London, GB; AN 95–048800 XP002069425 & JP 06 329 606 A (Nippon Shokubai Co. Ltd), Imino Di Succinic Acid Metal Salt Produce Useful Preparation Detergent Build Pigment Disperse Comprise React Maleic Acid Ammonia Add Alkali Alkaline Earth Hydroxide Age, Nov. 1994.

Database WPI, Sec. Ch, Wk 9616, Derwent Pub. London, GB; Class D25, AN 96–157376 XP002969426 & JP 08 041 490 A (Nippon Shokubai Co. Ltd), Build Contain Carboxylic Acid Ester Improve Biodegradable High Water Soluble Useful Surfactant Washing Power, Feb. 1996.

Database WPI, Sec. Ch, Wk 9613, Derwent Publ. London, Gb; Class D25, An 96–112673 XP002069427 & JP 08 012 631 A (Nippon Chem Ind Co Ltd) Preparation Alkali Metal Salt Imino Di Succinic Acid Comprise Add Hemi Ester Maleic Acid Aspartic Acid Ammonia Alkaline condition Biodegradable Chelate Agent, Jan. 1996.

Food: Disinfectants; Detergents—p. 37, Wk. 9507, JP 06 329 607, Nippon Shokubai Co Ltd, Production of imino–di:succinic acid metal salts for detergent builder, etc.—comprises reacting maleic acid cpd. with ammonia in aq. medium adding alkali metal hydroxide and adding maleic acid cpd, Nov. 1994.

*Primary Examiner*—Samuel Barts
*Attorney, Agent, or Firm*—Joseph C. Gil; Diderico van Eyl

[57] ABSTRACT

A process for the preparation of iminodisuccinic acid alkali metal salts by reaction of maleic acid and ammonia in an aqueous medium in the presence of alkali metal hydroxides and working up thereof.

9 Claims, No Drawings

PREPARATION AND USE OF
IMINODISUCCINIC ACID SALTS

BACKGROUND OF THE INVENTION

The invention relates to a process for the preparation of iminodisuccinic acid alkali metal salts by reaction of maleic acid and ammonia in an aqueous medium in the presence of alkali metal hydroxides and working up thereof. The resulting products can be employed as complexing agents for alkaline earth metal and heavy metal ions in the fields of detergents and cleaning compositions, pharmaceuticals, cosmetics, agriculture, electroplating, building materials, textiles and paper. In these fields, use as a water softener, bleaching agent stabilizer, trace nutrient fertilizer and setting retarder is to be emphasized in particular. The invention furthermore relates to the use of iminodisuccinic acid alkali metal salts in papermaking.

Complexing agents have been employed in large amounts for years. Many complexing agents customary to date, such as ethylenediaminetetraacetic acid (EDTA), diethylenetri-aminepentaacetic acid (DTPA), nitrilotriacetic acid (NTA) and various phosphonates, are not biodegradable or are biodegradable to only a limited degree, remobilize heavy metals in surface waters and can even enter drinking water treatment, since they are adsorbed neither in sewage sludges nor in soils. Phosphates are complexing agents which contribute towards eutrophication of surface waters. Summarizing, these are ecotoxicological properties which are found to be a disadvantage nowadays.

It is therefore an important object to develop complexing agents which do not have the ecotoxicological disadvantages to date. Iminodisuccinic acid is thus a complexing agent which shows a ready biodegradability and therefore has an ecotoxicological advantage over the complexing agents to date.

In the future, however, not only will the product properties of chemicals which chiefly enter the environment after use be examined critically under the aspects described, but also the preparation processes. It was thus surprising that an environmentally relevant preparation process could also be found for a chemical which is currently not yet available industrially and has environmentally relevant properties.

For iminodisuccinic acid, the following preparation possibilities based on maleic anhydride or maleic acid and ammonia are known to date: GB 1 306 331 describes the preparation of iminodisuccinic acid from maleic acid and ammonia in a molar ratio of 2:3 to 2:5 at temperatures of 60 to 155° C. For working up, either hydrochloric acid or sodium hydroxide solution are added. In SU 0 639 863, iminodisuccinic acid is prepared from maleic acid and ammonia at a molar ratio of 2:0.8 to 2:1 and temperatures of 110 to 130° C. in the presence of alkali metal hydroxides. JP 6/329 606 describes a three-stage process for the preparation of iminodisuccinic acid. A maleic acid derivative is first reacted with ammonia in an aqueous medium. Alkali metal or alkaline earth metal hydroxides are then added. In the third process stage, a so-called maturation process follows. JP 6/329 607 also describes a three-stage process for the preparation of iminodisuccinic acid. In the first stage, a maleic acid derivative is again first reacted with ammonia in an aqueous medium. Alkali metal or alkaline earth metal hydroxides are then added in the second stage. In the third stage, after addition of a further maleic acid derivative, the reaction is continued. It is expressly stated in this patent application that maleic anhydride, maleic acid or maleic acid ammonium salt are employed as maleic acid derivatives.

The desired reaction is said to take place hardly at all with metal salts of maleic acid, so that the aim cannot be achieved.

It is all the more astonishing that, according to the invention, maleic acid and ammonia can be reacted in an advantageous manner to give iminodisuccinic acid in high yields precisely in the presence of alkali metal hydroxides.

SUMMARY OF THE INVENTION

The invention therefore relates to a process for the preparation of iminodisuccinic acid alkali metal salts, which is characterized in that maleic anhydride (MA), alkali metal hydroxide (MeOH), ammonia ($NH_3$) and water are reacted in a molar ratio of $MA:McOH:NH_3:H_2O=2:0.1-4:1.1-6:5-30$ at temperatures of 70–170° C., under pressures of 1–80 bar over reaction times of 0.1–100 h, ammonia and water are distilled off from the reaction mixture at temperatures of 50–170° C. under pressures of 0.1–50 bar in the course of 0.1–50 h, with the addition of water and 0–4 mol of MeOH per 2 mol of MA originally employed, and after the distillation water is added in an amount such that the solution formed contains a solids content of 5–60%, based on the total weight of the solution.

DESCRIPTION OF THE INVENTION

In the process according to the invention, water, alkali metal hydroxide (MeOH), maleic anhydride (MA) and ammonia (NH3) are metered into a reactor and the maleic acid salt formed is reacted at the reaction temperatures (T) and over the reaction times (t) mentioned. Ammonia is then distilled off as a mixture with water, with the addition of water and, if appropriate, further MeOH. After this distillation, the product is adjusted to an expedient concentration by addition of water. If appropriate, this product solution can be subjected to a clarifying filtration. Me here denotes Li, Na or K, preferably Na or K, particularly preferably Na.

The process according to the invention has the advantage that it can be carried out both discontinuously and continuously, and a high degree of profitability can be achieved here. This state of affairs is of great importance, since in spite of all advantages, environmentally friendly products are also only competitive if they can be prepared under corresponding economic conditions. The process according to the invention produces no waste, since after distillation of the ammonia, which can be recycled and further processed and, if appropriate, employed again, the product which remains is used completely. According to OECD 301 E, this product is moreover readily biodegradable. Economy and ecology are combined with one another in the process and product in a hitherto unknown manner.

In the process according to the invention, MA, water and alkali metal hydroxide are first mixed with one another in a molar ratio of MA:MeOH:water=2:0.1–4:5–30, it being possible for different metering variants to be carried out. Thus, MA can first be converted into the corresponding maleic acid salts with water via the maleic acid stage, or alternatively directly with aqueous alkali metal hydroxide solution. The second metering variant has proved to be advantageous for technical and chemical reasons. With this it is possible to prepare particularly concentrated maleic acid salt solutions of low secondary component content in a simple manner. These slightly yellowish solutions contain the possible secondary components fumaric acid and malic acid in only small amounts. The maleic acid salt is thus used in the further process with yields of >92%, preferably >95%, particularly preferably >98% of the theoretical amount.

In respect of a continuous process procedure, continuous and simultaneous metering of MA and alkali metal hydroxide solutions into an initially introduced maleic acid salt solution has proved to be particularly advantageous. Even very pure and also colorless solutions can be obtained with equally high yields in this manner.

Preferably, MA and MeOH are employed in a molar ratio of 2:0.5–3.9, particularly preferably 2:0.9–3.5, especially preferably 2:1.5–3.1.

Preferably, MA and NH3 are employed in a molar ratio of 2:1.2–5.5, particularly preferably 2:1.5–4.5, especially preferably 2:1.9–3.5.

Preferably, MA and $H_2O$ are employed in a molar ratio of 2:5.5–25, particularly preferably 2:6–20, especially preferably 2:6.5–15.

The maleic acid salt is prepared from MA, MeOH and water at temperatures of at least 60° C., for example at 60–130° C., preferably at 70–120° C., particularly preferably at 80–115° C., at which rapid and complete reaction of the MA is ensured and at which a stirrability and pumpability of the mixture can be maintained. The maleic acid salt can thus be present as a suspension or solution, preferably as a solution, which furthermore can be stirred for several hours without noticeable losses in yield occurring.

To the maleic acid salt suspensions or solutions formed from MA, MeOH and water is added ammonia in a molar ratio of MA:ammonia=2:1.1–6, preferably 2:1.2–5.5, particularly preferably 2:1.5–4.5. The addition can equally be carried out both in a discontinuous and in a continuous process procedure.

The maleic acid salt solutions formed from MA, MeOH, ammonia and water are reacted at temperatures of 70–170° C., preferably at 80–160° C., particularly preferably at 85–150° C., especially preferably 90–145° C., over reaction times of 0.1–100 h, preferably 0.2–50 h, particularly preferably 0.3–25 h, especially preferably 0.5–20 h. The reaction can be carried out both in discontinuous and in continuous reactors.

The reaction is as a rule carried out under the pressure which is established automatically. Pressures of up to 50 bar, preferably up to 30 bar, particularly preferably up to 20 bar can occur here. The mixture can additionally be covered with a layer of inert gases, in particular in discontinuous reactors, in which case pressures of up to 80 bar are admissible.

A maleic acid conversion of >93%, preferably >95%, particularly preferably >98% of the theoretical conversion is achieved by the reaction conditions.

After the reaction, ammonia and water are distilled off from the reaction mixture, with the addition of water and 0–4 mol, preferably 0.5–3.5 mol, particularly preferably 0.7–3.0 mol, especially preferably 0.9–2.5 mol of MeOH per 2 mol of MA originally employed. The water and MeOH can be added before or during the distillation, both in the discontinuous and in the continuous process. The amount of water added is chosen, taking into account the water which unavoidably distils off with the NH3, such that a solids content of 75% by weight, preferably 70% by weight, particularly preferably 65% by weight, based on the total weight of the batch, is not exceeded in the work-up mixture which remains.

The distillation is carried out at temperatures of 50–170° C., preferably at 60–150° C., particularly preferably at 70–140° C., especially preferably 80–135° C., under pressures of 0.1–50 bar, preferably 0.5–20 bar, in the course of 0.1–50 h, preferably 0.3–30 h, particularly preferably 0.5–25 h, especially preferably 0.9–20 h. Very substantial removal of unreacted and hydrolyzable ammonia (for example by condensation of the amide nitrogen formed RCONH2+MeOH→RCOOMe+NH3 where R=the hydrocarbon radical of the carboxylic acid on which the compound is based) from the reaction mixture is achieved as a result, and this can subsequently be worked up and used for a further processing. A minimization of the nitrogen content in the product is furthermore achieved as a result, and during use an unnecessarily high introduction of nitrogen into surface waters is thus avoided. The content of free maleic acid which still remains after the reaction is also reduced further.

After the distillation, water is added in an amount such that the product solution formed has a solids content, calculated as the sum of all the alkali metal salts, of 5–60% by weight, preferably 10–58% by weight, particularly preferably 15–55% by weight. Thereafter, if required, a clarifying filtration can be carried out. Such solutions are virtually neutral in odor and stable to storage.

After the reaction and working up, iminodisuccinic acid and its salts (formula 1) are obtained in yields of >65%, preferably >70%, particularly preferably >74% of the theoretical yield. The sum of all the secondary components and their salts are present in amounts of <35%, preferably <30%, particularly preferably <26% of the theoretical amounts, where maleic acid and its salts (formula 2) are present in <7%, preferably <5%, particularly preferably <2% of the theoretical amount, fumaric acid and its salts (formula 3) are present in <20%, preferably <15%, particularly preferably <10% of the theoretical amount, malic acid and its salts (formula 4) are present in <7%, preferably <5%, particularly preferably <3% of the theoretical amount and aspartic acid and its salts (formula 5) are present in <25%, preferably <20%, particularly preferably <15% of the theoretical amount.

Formula 1

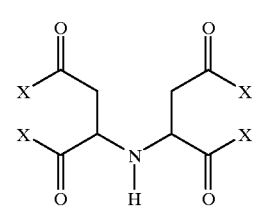

Formula 2

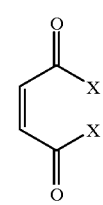

Formula 3

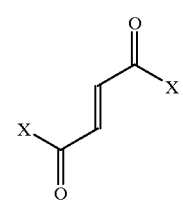

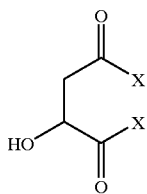

Formula 4

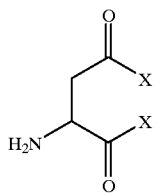

Formula 5

X=OH, OLi, ONa, OK, ONH4

Overall, product solutions in which the components of the formulae 1–5 mentioned are present in total yields of >93%, preferably >96%, particularly preferably >98% of the theoretical yield are obtained. According to the OECD 301 E test, the biodegradation of the products is more than 70%, usually more than 72%, often more than 74%, after 28 days.

The carboxyl groups of iminodisuccinic acid and its secondary components are present in acid or salt form, according to the amount of MeOH employed in the reaction and working up and the amount of ammonia distilled off during working up. Thus, in the case where Me=Na, iminodisuccinic acid can be obtained as the $Na_2$ to $Na_4$ salt, preferably as the $Na_3$ to $Na_4$ salt, particularly preferably as the $Na_4$ salt, the other carboxyl groups being present, as appropriate, as the free acid and as the ammonium salt. In the case where LiOH or KOH or a mixed MeOH is employed, the carboxyl groups are also present as the lithium or potassium salt.

The products prepared in the process according to the invention are distinguished by very low heavy metal contents. The contents of chromium, manganese, iron and nickel ions in total is thus less than 80 ppm, preferably less then 60 ppm, particularly preferably less than 30 ppm. The content of alkaline earth metal ions is less than 500 ppm, preferably less than 200 ppm, particularly preferably less than 100 ppm. The products are therefore distinguished as effective complexing agents for alkaline earth metal and heavy metal ions.

In the reaction, MA is employed in the form of a melt, flakes or briquettes, preferably a melt or flakes, and ammonia is employed in the liquid or gaseous form or as a solution in water, preferably in the liquid form or as a solution in water. Aqueous ammonia solutions are employed with contents of >15% by weight, preferably >20% by weight, particularly preferably >25% by weight of NH3. The alkali metal hydroxides MeOH are employed in the reaction and working up undiluted or in aqueous solution. Aqueous alkali metal hydroxide solutions are metered into the vessel in concentrations of 10–60% by weight, preferably 20–55% by weight, particularly preferably 25-50% by weight.

In a particular embodiment, MA melt is metered into aqueous sodium hydroxide solution at temperatures of >60° C. and liquid ammonia or concentrated aqueous ammonia solution is then added. The MA:NaOH:NH3:$H_2O$ molar ratio here is 2:1.5–3.5:1.5–3.5:6–20. The educts are reacted at temperatures of 90–145° C. over reaction times of 0.3–25 h. Water and ammonia are distilled off from the reaction mixture at temperatures of 80–135° C. in the course of 0.5–25 h, with the addition of water and 0.5–2.5 mol of NaOH per 2 mol of MA originally employed. After the addition of water, with which solids contents of 5–60% by weight are established and a clarifying filtration, product solutions which comprise iminodisuccinic acid in yields of >73%, maleic acids in amounts of <3%, fumaric acid in amounts of <10%, malic acid in amounts of <5% and aspartic acid in amounts of <15% of the particular theoretical yields or amounts are obtained.

In another particular embodiment, an MA melt and aqueous sodium hydroxide solution are metered simultaneously and continuously in a molar ratio of MA:NaOH:$H_2O$= 2:1.5–3.5:6–20 into a maleic acid salt solution or pumpable suspension, which has been initially introduced and is of like composition, at temperatures of 75-125° C. This solution or suspension is pumped, with residence times of 0.1–5 h, into a second mixer, into which liquid ammonia or a concentrated aqueous ammonia solution is added continuously. The molar ratio of MA:ammonia here is 2:1.5–3.5. This solution is reacted at temperatures of 90–145° C. and residence times of 0.3–25 h in a continuous reactor. Ammonia and water are distilled off from the reaction mixture in a continuous distillation column at temperatures of 70–140° C. and residence times of 0.1–25 h, with continuous addition of water and aqueous sodium hydroxide solution corresponding to 0.5–2.5 mol of NaOH per 2 mol of MA originally employed. After the addition of water, solutions with solids contents of 5–60% by weight are obtained, and are subjected to a clarifying filtration, if appropriate. The product solutions have yields of >73% of iminodisuccinic acid, <3% of maleic acid, <10% of fumaric acid, <5% of malic acid and <15% of the particular theoretical yields of aspartic acid.

In the process according to the invention, product solutions with a high iminodisuccinic acid yield and a high complexing capacity are obtained by reaction and working up. The secondary components impair neither the complexing capacity nor the biodegradation. The products are very substantially free from ammonia. They are virtually neutral in odor, stable to storage and largely free from troublesome alkaline earth metal and heavy metal ions. Secondary components occur by condensation to only a very minor extent and are additionally reduced in amount by the working up.

Iminodisuccinic acid alkali metal salts, in particular those prepared according to the invention, can be used to increase the degree of whiteness and the brightness of plant fibers in papermaking, for example in the processing of cellulose or wood pulp (thermomechanical pulp) in the pretreatment of fibers or in oxidative or reductive bleaching, for example with $H_2O_2$ or with sodium dithionite ($Na_2S_2O_4$), in particular in the pretreatment of fibers before the bleaching process or in reductive bleaching. The invention is further described in the following illustrative examples in which all parts and percentages are by weight unless otherwise indicated.

EXAMPLES

The yields and contents stated in the examples relate either to the MA employed or to the carbon determined by elemental analysis and have been obtained by the following analytical methods: maleic acid, fumaric acid and aspartic acid by liquid chromatography (HPLC), malic acid by capillary electrophoresis (CE) and iminodisuccinic acid by the calcium carbonate dispersing capacity (CCDC).

The CCDC value is measured at pH 11 in mg of $CaCO_3$ per g of solid. In the example of the iminodisuccinic acid $Na_4$ salt, the CCDC value gives the yield in a good approximation by the following equation: IDA $Na_4$ salt [% of the theoretical yield]=(CCDC−20):2.

For comparison, for citric acid $Na_3$ salt and ethylenediaminetetraacetic acid $Na_4$ salt CCDC values of 55 and 280 mg of $CaCO_3$ per g of substance result in this test. The test was carried out as follows:

1.5 g of the substance under investigation (in the case of the comparison substances based on 100% Na salt, in the case of the product solutions based on the solids content) are dissolved in 90 ml of water, the solution is preneutralized, if necessary, and 10 ml of a 10% strength by weight $Na_2CO_3$ solution are added. The solution is then adjusted to pH 11 and titrated at 25° C. with a 0.10 molar calcium acetate solution until clouding starts, this being generated by calcium carbont precipitating out. The titration is monitored with the aid of a light conductor photometer. The volume of calcium acetate consumed can be determined from the first turning point in the titration curve, and from this the amount of calcium ions bonded by the test substance (complexing agent) can be calculated. The amount of bonded calcium is stated as $CaCO_3$/g of test substance.

The product solutions prepared in the following examples are suitable as stabilizers for peroxo compounds in aqueous solution due to the complexing action. The stabilization is tested as follows on the example of hydrogen peroxide:

1.5 g of a 33.3% strength $H_2O_2$ solution are added to 98 g of distilled water. 50 mg of the stabilizer to be tested (based on 100% Na salt or solid) are added thereto. The mixture is then adjusted to pH 10.5 and subsequently heated at 80° C. for 35 minutes. Thereafter, the $H_2O_2$ content is determined iodometrically. For comparison, the residual $H_2O_2$ content is determined in a blank sample (without stabilizer) treated under identical conditions. The degree of stabilization is then determined as follows:

$((a-b)/(c-b)) \times 100$=stabilization [%] wherein a=$H_2O_2$ content in the stabilized sample after heating,
b=$H_2O_2$ content in the blank sample after heating and
c=initial content of $H_2O_2$ in the sample. The product prepared in Example 5 showed an $H_2O_2$ stabilization of 96% in this test.

Example 1

MA:NaOH:$NH_3$:$H_2O$ molar ratio=2:3:2:12.6, 100° C., 48 h.

A maleic acid Na salt solution which had been formed in sequence from 908 g=50.44 mol of water, 784 g=8 mol of MA and 480 g=12 mol of NaOH was initially introduced into a 3 liter autoclave, 136 g=8 mol of ammonia (liquid) were added at 90–100° C. and the mixture was stirred at 100° C. for 48 h. After dilution with water to 4000 g and after addition of 160 g=4 mol of NaOH, 2000 g of aqueous ammonia were distilled off from the reaction mixture at 70° C. under 240 mbar. The product solution was diluted with water to 4000 g and filtered. The solids content, which was taken as the basis for the CCDC value measurement, was 33.7% by weight. The following yields (% of theory) were obtained: 0.1% of maleic acid, 5.6% of fumaric acid, 77.5% of iminodisuccinic acid and 14.6% of aspartic acid.

Example 2

MA:NAOH:$NH_3$:$H_2O$ molar ratio=2:3:2:12.6, 110° C., 12 h.

A maleic acid Na salt solution which had been formed in sequence from 227 g=12.61 mol of water, 196 g=2 mol of MA flakes and 120 g=3 mol of NaOH was initialy introduced into a 0.7 liter autoclave, 34 g=2 mol of ammonia (liquid) were added at 90–100° C. and the mixture was stirred at 110° C. for 12 h. After dilution with water at 70° C. and after addition of 40 g=1 mol of NaOH, 500 g of ammonia and water were distilled off from the reaction mixture at 70° C. under 240 mbar. The product solution was diluted with water to 1500 g and filtered. The solids content was 22.5% by weight. The following yields (% of theory) were obtained: 1.7% of maleic acid, 7.7% of fumaric acid, 78.5% of iminodisuccinic acid and 11.7% of aspartic acid.

Example 3

MA:NaOH:$NH_3$:$H_2O$ molar ratio=2:3:2:12.6, 120° C., 6 h.

The metering sequence, the metered amounts and the working up corresponded to Example 2. The reaction mixture was stirred at 120° C. for 6 h. The product solution was diluted with water to 1500 g and filtered. The solids content was 22.5% by weight. The following yields (% of theory) were obtained: 2.0% of maleic acid, 8.5% of fumaric acid, 74.5% of iminodisuccinic acid and 11.4% of aspartic acid.

Example 4

MA:NaOH:$NH_3$:$H_2O$ molar ratio=2:3:2:12, 120° C., 6 h 196 g=2 mol of MA melt and 210 g=2.625 mol of 50% strength sodium hydroxide solution were metered simultaneously at 60–70° C. into an initial amount of 30 g=0.375 mol of 50% strength sodium hydroxide solution. After a clear solution had been obtained at 100° C., 130 g=2 mol of 26.2% strength aqueous ammonia solution were added thereto, cooling to 65° C. taking place. The solution was then stirred in a 0.7 liter autoclave at 120° C. for 6 h. After addition of 250 g of water and 80 g=1 mol of 50% strength sodium hydroxide solution, ammonia and water were distilled off at temperatures of 94–111° C. The product was diluted with water to 850 g and filtered. The solids content was 39.6% by weight. The following yields (% of theory) were obtained: 2.1% of maleic acid, 9.0% of fumaric acid, 79.5% of iminodisuccinic acid and 10.1% of aspartic acid.

Example 5

MA:NaOH:$NH_3$:$H_2O$ molar ratio=2:3:2:12, 120° C., 6 h.

240 g=3 mol of 50% strength sodium hydroxide solution were initially introduced into the reaction vessel and heated to 60° C. 196 g=2 mol of MA melt were metered in at 70° C. After a solution had been obtained at 100° C., 130 g=2 mol of 26.2% strength aqueous ammonia solution were added at 60–70° C. The resulting solution was stirred in a 0.7 liter autoclave at 120° C. for 6 h. After addition of 200 g of water and 80 g=1 mol of 50% strength sodium hydroxide solution, 220 g of ammonia and water were distilled off at 75° C. under 240 mbar. The product was diluted with water to 750 g and filtered. The solids content was 44.9% by weight. The following yields (% of theory) were obtained: 2.1% of maleic acid, 8.3% of fumaric acid, 76.0% of iminodisuccinic acid and 11.0% of aspartic acid.

Example 6

MA:NaOH:$NH_3$:$H_2O$ molar ratio=2:3:2:12.6, 120° C., 6 h.

250 kg=2.55 kmol of MA flakes were metered into a initial mixture of 19 kg of water and 306 kg=3.825 kmol of 50% strength sodium hydroxide solution. After addition of 162 kg=2.57 kmol of 27% strength aqueous ammonia solution, the mixture was stirred at 120° C. for 6 h. 450 kg of ammonia and water were distilled off at 70–80° C. under 300 mbar, with the addition of 102.5 kg=1.28 kmol of 50% strength sodium hydroxide solution and 755 kg of water. After the filtration, 1144.5 kg of product solution with a solids conent of 37.5% by weight and yields (% of theory) of 2.5% of maleic acid, 9.2% of fumaric acid, 4.1% of malic acid, 77.0% of iminodisuccinic acid and 10.0% of aspartic acid were obtained. In OECD 301 E, the product showed a biodegradation of 80% after 28 d.

Example 7

$MA:NaOH:NH_3 H_2O$ molar ratio=2:3:2:6.7, 120° C., 3 h.

196 g=2 mol of MA melt were metered at temperatures of >75° C. into an initial amount of 240 g=3 mol of 50% strength sodium hydroxide solution. After addition of 34 g=2 mol of ammonia (liquid), the reaction mixture was stirred at 120° C. for 3 h. After addition of 730 g of water and 40 g=1 mol of NaOH, 500 g of water and ammonia were distilled off at 70° C. under 240 mbar. The product was diluted with water to 1000 g and filtered. The solids content was 33.7% by weight. The following yields (% of theory) were obtained: 5,9% of maleic acid, 7.5% of fumaric acid, 78.5% of iminodisuccinic acid and 8.4% of aspartic acid.

Example 8

$MA:NaOH:NH_3:H_2O$ molar ratio=2:3:2:6.7, 120° C., 3 h.

196 g=2 mol of MA were dissolved in 120 g=6.7 mol of water. After addition of 120 g=3 mol of NaOH and 34 g=2 mol of ammonia, the mixture was stirred at 120° C. for 3 h. After dilution with water to 1200 g and addition of 40 g=[lacuna] NaOH, 500 g of ammonia and water were distilled off at 70° C. under 240 mbar. The product was diluted with water to 1000 g and filtered. The solids content was 33.7% by weight. The following yields (% of theory) were obtained: 4.7% of maleic acid. 8.8% of flumaric acid, 77.5% of iminodisuccinic acid and 8.6% of aspartic acid.

Example 9

$MA:NaOH:NH_3:H_2O$ molar ratio=2:4:2:12.6, 100° C., 96 h.

196 g=2 mol of MA were dissolved in 227 g=12.6 mol of water. After addition of 160 g=4 mol of NaOH and 34 g=2 mol of ammonia, the mixture was stirred at 100° C. for 96 h. After dilution with water to 1200 g, 500 g of ammonia and water were distilled off at 70° C. under 240 mbar. The product was diluted with water to 1500 g and filtered. The solids content was 22.5% by weight. The following yields (% of theory) were obtained: 2.7% of maleic acid, 5.6% of fumaric acid, 80.5% of iminodisuccinic acid and 7.3% of aspartic acid.

Example 10

$MA:NaOH:NH_3:H_2O$ molar ratio=2:2:2:12.6, 110° C., 12 h.

196 g=2 mol of MA were dissolved in 227 g=12.6 mol of water. After addition of 80 g=2 mol of NaOH and 34 g=2 mol of ammonia, the mixture was stirred at 10° C. for 12 h. After dilution with water to 1200 g and addition of 80 g=2 mol of NaOH, 500 g of ammonia and water were distilled off at 70° C. under 240 mbar. The product was diluted with water to 1000 g and filtered. The solids content was 33.7% by weight. The following yields (% of theory) were obtained: 0.5% of maleic acid, 6.7% of fumaric acid, 77.0% of iminodisuccinic acid and 11.8% of aspartic acid.

Example 11

$MA:NaOH:NH_3:H_2O$ molar ratio=2:2:2:12.6, 120° C., 3 h.

196 g=2 mol of MA were dissolved in 227 g=12.6 mol of water. After addition of 80 g=2 mol of NaOH and 34 g=2 mol of ammonia, the mixture was stirred at 120° C. for 3 h. After dilution with water to 1200 g and addition of 80 g=2 mol of NaOH, 500 g of ammonia and water were distilled off at 70° C. under 240 mbar. The product was diluted with water to 1000 g and filtered. The solids content was 33.7% by weight. The following yields (% of theory) were obtained: 2.7% of maleic acid, 7.2% of fumaric acid, 75.0% of iminodisuccinic acid and 11.9% of aspartic acid.

Example 12

$MA:NaOH:NH_3:H_2O$ molar ratio=2:2:3:12.6, 100° C., 24 h.

196 g=2 mol of MA were dissolved in 227 g=12.6 mol of water. After addition of 80 g=2 mol of NaOH and 51 g=3 mol of ammonia, the mixture was stirred at 100° C. for 24 h. After dilution with water to 1200 g and addition of 80 g=2 mol of NaOH, 500 g of ammonia and water were distilled off at 70° C. under 240 mbar. The product was diluted with water to 1500 g and filtered. The solids content was 22.5% by weight. The following yields (% of theory) were obtained: 0.6% of maleic acid, 4.5% of fumaric acid, 79.5% of iminodisuccinic acid and 15.4% of aspartic acid.

Example 13

$MA:NaOH:NH_3:H_2O$ molar ratio=2:2:4:12.6, 100° C., 12 h.

196 g=2 mol of MA were dissolved in 227 g=12.6 mol of water. After addition of 80 g=2 mol of NaOH and 68 g=3 mol of ammonia, the mixture was stirred at 100° C. for 12 h. After dilution with water to 1200 g and addition of 80 g=2 mol of NaOH, 500 g of ammonia and water were distilled off at 70° C. under 240 mbar. The product was diluted with water to 1500 g and filtered. The solids content was 22.5% by weight. The following yields (% of theory) were obtained: 3.4% of maleic acid, 4.5% of fumaric acid, 76.5% of iminodisuccinic acid and 14.5% of aspartic acid.

Example 14

$MA:NaOH:NH_3:H_2O$ molar ratio=2:2:2:10, 120° C., 3.5 h.

196 g=2 mol of MA melt were pumped at temperatures of >75° C. into an initial mixture of 180 g=10 mol of water and 80 g=2 mol of NaOH in an autoclave. After addition of 34 g=2 mol of ammonia, the mixture was stirred at 120° C. for 3.5 h. 200 g of water and 80 g=2 mol of NaOH were added to the reaction mixture and about 130 g of ammonia and water were distilled off. During this operation, the temperature rose. 100 g of water were added thereto at 110° C. under normal pressure in the course of 1 h and distillation off was repeated. The virtually odour-free product was diluted with water to 800 g and filtered. The solids content was 42.1% by weight. The following yields (% of theory) were obtained: 0.6% of maleic acid, 6.7% of fumaric acid, 75.5% of iminodisuccinic acid and 13.3% of aspartic acid.

Example 15

$MA:NaOH:NH_3:H_2O$ molar ratio=2:2:2:10, 110° C., 7 h.

196 g=2 mol of MA melt were pumped at temperatures of >75° C. into an initial mixture of 180 g=10 mol of water and 80 g=2 mol of NaOH in an autoclave. After addition of 34 g=2 mol of ammonia, the mixture was stirred at I 110° C. for 7 h. 200 g of water and 80 g=2 mol of NaOH were added to the reaction mixture, and about 130 g of ammonia and water were distilled off. During this operation, the temperature rose. 100 g of water were added thereto at 110° C. under normal pressure in the course of 1 h and distillation off was repeated. The virtually odour-free product was diluted with water to 800g and filtered. The solids content was 42.1% by weight. The following yields (% of theory) were obtained: 1.3% of maleic acid, 5.9% of fumaric acid, 80.0% of iminodisuccinic acid and 11.2% of aspartic acid.

Example 16

MA:NaOH:NH$_3$:H$_2$O molar ratio=2:2:2:10, 130° C., 1.5 h.

196 g=2 mol of MA melt were pumped at temperatures of >75° C. into an initial mixture of 180 g=10 mol of water and 80 g=2 mol of NaOH in an autoclave. After addition of 34 g=2 mol of ammonia, the mixture was stirred at 130° C. for 1.5 h. 200 g of water and 80 g=2 mol of NaOH were added to the reaction mixture, and about 130 g of ammonia and water were distilled off. During this operation, the temperature rose. 100 g of water were added at 110° C. under normal pressure in the course of 1 h and distillation off was repeated. The virtually odour-free product was diluted with water to 800 g and filtered. The solids content was 42.1% by weight. The following yields (% of theory) were obtained: 0.6% of maleic acid, 6.5% of fumaric acid, 75.0% of iminodisuccinic acid and 15.6% of aspartic acid.

Example 17

355 g/h=3.62 mol/h of MA and 501 g/h=3.86 mol/h of 30.8% strength by weight sodium hydroxide solution were metered simultaneously and continuously into an initial maleic acid Na salt solution of the composition to be prepared in a 1 liter stirred tank reactor, while cooling at a temperature of 118° C. The solution formed was pumped continuously into a cascade of stirred tanks comprising three reactors with a total volume of 7.4 liters. 68 g/h=4 mol/h of gaseous ammonia were admixed in the first reactor of the cascade. The temperature of the reaction solution was kept at 109–114° C. The reaction product was then mixed continuously with 991 g/h=3.92 mol/h of 15.8% strength by weight sodium hydroxide solution in a static mixer. Thereafter, the solution was passed to the top of a bubble tray column comprising ten trays and operated with about 520 g/h of stripping steam. 1037 g/h of ammonia and water were distilled off at a bottom temperature of 112° C., an overhead temperature of 101° C. and a liquid volume of about 1.3 liters, and 1398 g/h of product solution were obtained. The solids content was 43.8% by weight. The following yields (% of theory) were obtained. 2.3% of maleic acid, 9.2% of fumaric acid, 77.0% of iminodisuccinic acid and 11.5% of aspartic acid.

Use Example 1

Increasing the degree of whiteness and brightness in the oxidative bleaching of wood pulp (thermo-mechanical pulp) by using the product from Example 6 in the pretreatment.

The wood pulp was beaten at a pulp density of 4% in a disintegrator at 3000 rpm for 10 min. The product from Example 6 was added as a 1.3% strength by weight solution, based on the solids, to the stirred suspension. The amount of solids (=total of all the Na salts) here corresponded to 0.13–0.52%, based on the oven-dried (odr) fibrous material. The action time was 30 min at a temperature of 80° C. Dewatering to the pulp density of 25% required for the bleaching operation was carried out by means of a laboratory filter press. A portion of the complexed heavy metal ions was separated off from the fibrous material via the filtrate as a result. 0.7% of NaOH as a 1% strength by weight solution and 2% of hydrogen peroxide as a 20% strength by weight solution, based on the odr fibrous material, were added to the resulting fibrous material. Intensive thorough mixing and uniform distribution were achieved by means of a laboratory mixer. The bleaching time was 2.5 h at 60° C. After the bleaching, specimen sheets were produced with a Rapid-Köthen sheet former and the degree of whiteness and brightness were determined in accordance with DIN 53.145 and 53.140 respectively. For comparison, an experiment was carried out without the 5 addition of a complexing agent in the pretreatment. The following results were obtained.

| Addition of product from Example 6; solids [%], based on the odr fibrous material | Degree of whiteness [%] | Brightness [%] |
| --- | --- | --- |
| 0.00 | 57.4 | 71.2 |
| 0.13 | 57.7 | 72.3 |
| 0.26 | 58.8 | 73.6 |
| 0.39 | 60.5 | 75.3 |
| 0.52 | 61.9 | 76.6 |

In the presence of the product from Example 6, a significant increase in the degree of whiteness and brightness is to be found.

Use Example 2

Increasing the degree of whiteness and brightness in the oxidative bleaching of wood pulp (thermo-mechanical pulp) by using the product from Example 6:

The wood pulp was beaten as in Use Example 1 at a pulp density of 4% in a disintegrator at 3000 rpm. After an action time of 30 min at 80° C., the suspension was concentrated to a pulp density of 25% by means of a laboratory filter press. 0.7% of NaOH as a 1% strength solution, 2% of hydrogen peroxide as a 20% strength solution and 0.13–0.52% of product (corresponds to the solids) from Example 6 as a 1.3% strength solution were added to the resulting fibrous material. The amount employed in each case is based on the odr fibrous material. Intensive thorough mixing and uniform distribution was achieved by means of a laboratory mixer. The bleaching time was 2.5 h at 60° C. After the bleaching, specimen sheets were produced with a Rapid-Köthen sheet former and the degree of whiteness and brightness were determined in accordance with DIN 53.145 and 53.140 respectively. For comparison, a bleaching experiment was carried out without complexing agent. The following results were obtained:

| Addition of product from Example 6; solids [%], based on the odr fibrous material | Degree of whiteness [%] | Brightness [%] |
| --- | --- | --- |
| 0.00 | 57.4 | 71.2 |
| 0.13 | 58.7 | 72.2 |
| 0.26 | 59.5 | 73.2 |
| 0.39 | 60.4 | 74.3 |
| 0.52 | 61.0 | 75.0 |

In the presence of the product from Example 6, a significant increase in the degree of whiteness and brightness is to be found.

Use Example 3

Increasing the degree of whiteness in the reductive bleaching of wood pulp (thermo-mechanical pulp) by using the product from Example 6:

0.26–0.52% of product (corresponds to the solids) from Example 6 and, with exclusion of air, 1.0–1.5% of technical-grade sodium dithionite (approx. 85% strength) were added to the wood pulp at a pulp density of 4% at 60° C. The amount employed in each case is based on the odr fibrous material. After a bleaching time of 1 h at 60° C. (bag bleaching) and a pH of 6.0, the degree of whiteness of the TMP was determined. For comparison, a bleaching experiment was carried out without complexing agent. The following results were obtained:

| Addition of product from Example 6; solids [%], based on the odr fibrous material | Degree of whiteness [%] at 1.0% of $Na_2S_2O_4$ | Degree of whiteness [%] at 1.5% of $Na_2S_2O_4$ |
|---|---|---|
| 0.00 | 52.3 | 53.1 |
| 0.26 | 53.6 | 54.3 |
| 0.39 | 54.0 | 54.1 |
| 0.52 | 53.8 | 53.9 |

In the presence of the product from example 6, an increase in the degree of whiteness is to be found.

Although the present invention has been described in detail with reference to certain preferred versions thereof, other variations are possible. Therefore, the spirit and scope of the appended claims should not be limited to the description of the versions contained therein.

What is claimed is:

1. Process for the preparation of iminodisuccinic acid alkali metal salts, wherein maleic anhydride (MA), alkali metal hydroxide (MeOH), ammonia ($NH_3$) and water are reacted in a molar ratio of MA:MeOH:$NH_3$:$H_2O$= 2:0.1–4:1.1–6:5–30 at temperatures of 70–170° C., under pressures of 1–80 bar over reaction times of 0.1–100 h, ammonia and water are distilled off from the reaction mixture at temperatures of 50–170° C. under pressures of 0.1–50 bar in the course of 0.1–50 h, with the addition of water and 0–4 mol of MeOH per 2 mol of MA originally employed, and after the distillation water is added in an amount such that the solution formed contains a solids content of 5–60%, based on the total weight of the solution.

2. Process according to claim 1, wherein MA, MeOH, ammonia and water are reacted at temperatures of 80–160° C.

3. Process according to claim 1, wherein, after the reaction, ammonia and water are distilled off with the addition of water and 0.5–3.5 mol of MeOH per 2 mol of MA originally employed.

4. Process according to claim 1, wherein, after the reaction, ammonia and water are distilled off at temperatures of 60–150° C. under pressures of 0.5–20 bar in the course of 0.3–30 h.

5. Process according to claim 1, wherein, after the distillation of ammonia and water, the product solution is adjusted to solids contents, calculated as the sum of all the alkali metal salts, of 10–58% by weight, by addition of water and, if appropriate, is subjected to a clarifying filtration.

6. Process according to claim 1, wherein NaOH is employed in an amount such that iminodisuccinic acid $(Na)_2$ to $(Na)_4$ salts, preferably $(Na)_3$ to $(Na)_4$ salts, particularly preferably $(Na)_4$ salts, are obtained, the other carboxyl groups being present, if appropriate, as the free acid and as the lithium, potassium or ammonium salt.

7. Process according to claim 1, wherein the process steps of reaction and working up and the associated meterings of the components can be carried out both discontinuously and continuously.

8. Process according to claim 1, wherein aqueous sodium hydroxide solution, MA and ammonia or an aqueous ammonia solution in a molar ratio of MA:NaOH:$NH_3$:water= 2:1.5–3.5:1.5–3.5:6–20 are metered in sequence into a reactor and are reacted at temperatures of 90–145° C. with reaction times of 0.3–25 h, ammonia and water are distilled off at temperatures of 80–135° C. in the course of 0.5–25 h, with the addition of water and 0.5–2.5 mol of NaOH per mol of MA originally employed, and, after the distillation, water is added in an amount such that the solution formed contains a solids content of 5 to 60%, based on the total weight of the solution.

9. Process according to claim 1, wherein MA and aqueous sodium hydroxide solution are metered simultaneously and continuously in a molar ratio of MA:NaOH:$H_2O$= 2:1.5–3.5:6–20 into an initially introduced maleic acid salt solution of corresponding composition, after residence times of 0.1–5 h ammonia or aqueous ammonia solution is added to this solution in a separate mixer in a molar ratio of MA:$NH_3$=2:1.5–3.5, the resulting solution is reacted in a continuous reactor under residence times of 0.3–25 h at temperatures of 90–145° C., ammonia and water are distilled off continuously from the reaction mixture, with continuous addition of water and 0.5–2.5 mol of NaOH per 2 mol of MA originally employed, and, after the distillation, water is added continuously in an amount such that the resulting solution contains a solids content of 5–60%, based on the total weight of the solution.

* * * * *

UNITED STATES PATENT AND TRADEMARK OFFICE
CERTIFICATE OF CORRECTION

PATENT NO. : 6,107,518
DATED : August 22, 2000
INVENTOR(S) : Torsten Groth et al It is certified that error appears in the above-indentified patent and that said Letters Patent is hereby corrected as shown below:

Column 2, line 14, delete "McOH" and insert --MeOH--.

Column 9, line 60, delete "10°C" and insert --110°C--.

Column 11, line 2, delete "I".

Column 12, line 14, delete "5".

Signed and Sealed this

First Day of May, 2001

*Attest:*

NICHOLAS P. GODICI

*Attesting Officer*  *Acting Director of the United States Patent and Trademark Office*